United States Patent [19]

Miyake et al.

[11] E Patent Number: Re. 33,047

[45] Reissued Date of Patent: Sep. 5, 1989

[54] PROCESS FOR PRODUCING A HIGH-PURITY MALTOSE

[75] Inventors: Toshio Miyake; Shuzo Sakai; Takashi Shibuya, all of Okayama, Japan

[73] Assignee: Kabusihiki Kaisha Hayashibara Seibutsu Kagaku Kenkyujo, Okayama, Japan

[21] Appl. No.: 202,249

[22] Filed: Jun. 6, 1988

Related U.S. Patent Documents

Reissue of:

[64] Patent No.: 4,487,198
Issued: Dec. 11, 1984
Appl. No.: 402,823
Filed: Jul. 28, 1982

[30] Foreign Application Priority Data

Aug. 3, 1981 [JP] Japan ..... 56-121725

[51] Int. Cl.[4] ..... C13D 3/14; C13K 7/00

[52] U.S. Cl. ..... 127/46.3; 127/46.2; 127/30; 435/95

[58] Field of Search ..... 127/46.3, 46.2, 29, 127/30, 32, 69; 435/99, 95, 100

[56] References Cited

U.S. PATENT DOCUMENTS

| | | | |
|---|---|---|---|
| 3,565,765 | 2/1971 | Heady | 435/95 |
| 3,795,584 | 3/1974 | Mitsuhashi | 435/95 |
| 3,817,787 | 6/1974 | Hertzen | 127/46.3 |
| 3,832,285 | 8/1974 | Kurimoto | 435/95 |
| 4,022,637 | 5/1977 | Sutthoff | 127/46.2 |
| 4,294,623 | 10/1981 | Hidaka | 435/95 X |
| 4,384,898 | 5/1983 | Okada | 435/95 X |
| 4,391,649 | 7/1983 | Shimizu et al. | 127/46.2 |

FOREIGN PATENT DOCUMENTS

| | | | |
|---|---|---|---|
| 52-46290 | 11/1977 | Japan . | |
| 55-85395 | 6/1980 | Japan | 435/100 |
| 51-86143 | 7/1986 | Japan | 127/46.2 |
| 1048 | of 1881 | United Kingdom | 435/100 |
| 1373529 | 11/1974 | United Kingdom . | |
| 1426976 | 3/1976 | United Kingdom | 435/95 |

*Primary Examiner*—Kenneth M. Schor
*Attorney, Agent, or Firm*—Browdy and Neimark

[57] ABSTRACT

High-purity maltose is produced by applying a feed starch sugar solution with a maltose content of at least 70% to a column packed with a strongly-acidic cation exchange resin of alkali metal- or alkaline earth metal-form; fractionating the feed solution by charging water thereto in a high-dextrin fraction, a high-dextrin.maltose fraction, a high-maltose fraction, a high-maltose.-glucose fraction, and a high-glucose fraction, in the given order; and recovering the high-maltose fraction. This process constantly provides a fraction with a maltose content of 93% or higher, and enables industrial-scale production of a high-purity maltose much easier and at lower-cost than conventional processes.

7 Claims, 1 Drawing Sheet

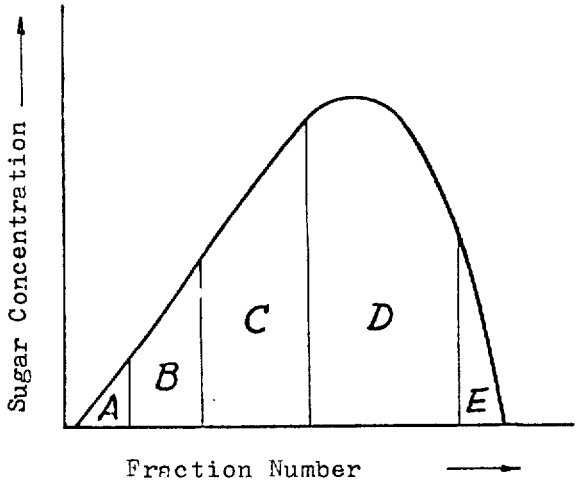
Sugar Concentration
A
B
C
D
E
Fraction Number

PROCESS FOR PRODUCING A HIGH-PURITY MALTOSE

Matter enclosed in heavy brackets [ ] appears in the original patent but forms no part of this reissue specification; matter printed in italics indicates the additions made by reissue.

BACKGROUND OF THE INVENTION

The present invention relates to a process for producing a high-purity maltose.

Recently, various advantages of maltose in food products and pharmaceuticals have been established one after another. Thus it uses have expanded rapidly. These expanded uses have inevitably led to increasing demands for a high-purity maltose.

Conventionally, maltose, has been available as a saccharified starch product with a maltose content of about 40–50 w/w % based upon the weight of the dry solid solute (all percentages are used in the specification mean "weight percentages on dry solid basis" unless otherwise specified) which is obtainable by subjecting a liquefied starch solution to the action of a malt enzyme.

Recent advances in starch saccharifiction techniques have somewhat simplified the production of a saccharified starch product with a maltose content of 50% or higher, for example, by the combined treatment of starch with $\beta$-amylase and starch debranching enzyme.

The above described starch saccharification technique, however, from economical and technical standpoints, renders the direct production of a high-purity maltose with a maltose content of 90% or higher very difficult.

Some processes for obtaining a high-purity maltose are disclosed in recent patent applications. In some of these process, a starch sugar solution containing maltose is passed through a column of an anion exchange resin. For example, Japanese Patent Publication No. 46,290/77 discloses a process for producing a high-purity maltose comprising preparing a starch sugar solution substantially consisting of dextrin and about 65% maltose, and applying the solution to an anion exchange resin of OH-form to adsorb the maltose constituent and also to remove the dextrin constituent. Since, however, in such a process the maltose constituent is adsorbed on the anion exchange resin of OH-form, the solution should be applied to the resin at the lowest possible temperature, preferably, below 20° C., to prevent the isomerization of the maltose constituent. Thus, increased viscosity and microbial contamination as well as low purification capability result, rendering its industrial-scale practice very difficult. Further, Japanese Patent Publication No. 20,579/79 discloses a process for producing a high-purity maltose which comprises applying a starch sugar solution, containing glucose and maltose, to a column packed with an anion exchange resin of $SO_3^{2-}$- or $SO_3H^-$-form, to fractionate the solution into the glucose- and maltose-constituents. The process is, however, inadequate as a process for industrial-scale production of a high-purity maltose because the bonding of the $SO_3^{2-}$- or $SO_3H^-$-group is labile.

SUMMARY OF THE INVENTION

The present inventors have investigated processes for producing a high-purity maltose using a strongly-acidic cation exchange resin, more particularly, of alkali metal- or alkaline earth metal-form, instead of an anion exchange resin which has the above described disadvantages. These efforts resulted in the finding that a high-purity maltose is easily obtainable by admitting a feed starch sugar solution with a maltose content of at least 70% and water to a column packed with a strongly-acidic cation exchange resin of alkali metal- or alkaline earth metal-form thereby fractionating the solution into a high-dextrin fraction, a high-dextrin, maltose fraction, a high-maltose fraction, a high-maltose.-glucose fraction, and a high-glucose fraction (the terms "high-A fraction" and "high-A.B fraction" as used in the specification shall mean the eluted fractions rich in A, or rich in A but highly contaminated with B); and recovering the high-maltose fraction.

Also, these efforts have resulted in the additional finding that high-purity maltose is constantly obtainable in higher concentration and at higher recovery yield by employing a method where the feed starch sugar solution is applied to the column together with the previously obtained high-dextrin.maltose- and/or high-maltose.glucose-fractions, and wherein the resultant high-dextrin.maltose-and/or high-maltose.glucose fractions are admitted to the column together with a fresh feed starch sugar solution in the next fractionation step.

BRIEF DESCRIPTION OF THE DRAWING

The drawing shows the elution pattern of the feed solution upon the fractionation into fractions A through E, i.e., the high-dextrin fraction, high-dextrin.maltose fraction, high-maltose fraction, high-maltose.glucose fraction, and high-glucose fraction, respectively.

The above described findings led to the present invention.

DETAILED DESCRIPTION OF THE INVENTION

The feed starch sugar solution usable in the present invention may be almost any substantially-ketose-free solution of aldoses derived from starch. Such a feed solution results in a high-maltose fraction; and with a maltose content of 90%, typically 93% or higher, in a high yield when subjected to the fractionation according to the present invention. For example, feed starch sugar solution may be a saccharified starch solution obtained by subjecting starch to the actions of starch-degrading enzymes, e.g., $\alpha$- and $\alpha$-amylases, and starch-debranching enzyme, or may be an aqueous solution of a commercially-available starch sugar product having a maltose content of at least 70%.

The strongly-acidic cation exchange resin of alkali metal- or alkaline earth metal-form usable in the invention may be, for example, one or more members of styrene-divinylbenzene copolymer resins bearing sulphonyl groups of alkali metal- or alkaline earth metal-form, such as $Na^+$, $K^+$, $Ca^{2+}$, or $Mg^{2+}$. Commercially-available resins are, for example, "Dowex 50WX2", "Dowex 50WX4", and "Dowex 50WX8", products of Dow Chemical Company, Midland, Mich., U.S.A., "Amberlite CG-120", a product of Rohm & Haas Company, Philadelphia, Pa. , U.S.A., "XT-1022E", a product of Tokyo Chemical Industries, Kita-ku, Tokyo, Japan, and "Diaion SK 1B", "Diaion SK 102", and "Diaion SK 104", products of Mitsubishi Chemical Industries Limited, Tokyo, Japan. All of these resins have excellent fractionating capability to obtain the high-maltose fraction, and are highly heat- and abrasion-resitant. Thus, they are advantageously useful for producing a high-purity maltose on an industrial-scale.

In the process according to the present invention, a resin with a nominal particle size of about 0.01–0.5 mm is packed in one or more columns. The bed depth preferred in the invention is generally 7 m or longer. If two or more columns are used, they are cascaded to give a total bed depth of 7 m or longer.

As to the column usable in the present invention, any column can be used regardless of its material, size, and shape so far as the objectives of the invention can be attained therewith. The column may be, for example, of glass, plastic or stainless steel, and its shape may be, for example, in cylindrical or square pillar form, but it should be designed to give the most effective laminar flow possible when the feed starch sugar solution is applied to the column packed with the resin.

The following description concretely explains in detail the method of the present invention.

One or more column(s) is packed with a strongly-acidic cation exchange resin of alkali metal- or alkaline earth metal-form, in an aqueous suspension, to give a total bed depth of 7 m or longer. While keeping the temperature in the column(s) at 45°–85° C., the feed starch sugar solution, at a concentration of about 10–70 w/w %, in an amount of about 1–60 v/v % against the bed volume, is admitted into the column(s) and then charged upwards or downwards with water at a flow rate of about SV 0.1–2.0 to effect fractionation of the material starch sugar solution into a high-dextrin fraction, a high-dextrin.-maltose fraction, a high-maltose fraction, a high-maltose.glucose fraction, and a high-glucose fraction, in the given order. The high maltose-fraction is then recovered.

Although the eluted fractions are generally collected in about 1–20 v/v % against the bed volume, they may be distributed automatically into the fractions.

When the feed starch sugar solution is admitted into the column prior to, after, or together with the previously obtained high-dextrin.maltose- and/or high-maltose.glucose-fractions, the amount of water required for substantial fractionation of the feed starch sugar solution can be sharply reduced, and the maltose constituent in the solution can be recovered in higher purity, higher concentration, and higher yield. Preferably, the previously obtained high-dextrin.maltose fraction, the feed starch sugar solution, and the previoiusly obtained high-maltose.glucose fraction are applied successively to the column in the given order.

Although the high-maltose fraction thus obtained can be used intact, it may be, if necessary, treated further as follows. The high-maltose fraction may be subjected to conventional purification steps, e.g., filtration, decolorization and/or deionization. Then, the purified product is, for example, concentrated to obtain a syrup, or crystallized to obtain a mascuit which may be spray-dried into crystalline powder, or separated into mother liquor and maltose crystals of much higher purity.

The high-purity maltose thus obtained is extremely useful in various applications, e.g., for production of food products or pharmaceuticals.

The following experiments explain the present invention in more detail.

EXPERIMENT 1

Feed starch sugar solution

The feed starch sugar solutions used in this experiment were prepared from commercially-available starch sugar products as listed in Table I, products of Hayashibara Company, Limited, Okayama, Japan, by dissolving or diluting them in water to give respective concentrations of 45 w/w %.

"Dowex 50WX4 (NA+)", a commercially-available strongly-acidic cation exchange resin of alkali metal-form, a product of Dow Chemical Company, Midland, Mich., U.S.A., in an aqueous suspension, was packed in a jacketted stainless steel column, inside diameter, 5.4 cm, to give a bed depth of 10 m.

While keeping the temperature in the column at 75° C., each feed starch sugar solution listed in Table I was admitted to the column in an amount of 5 v/v % against the bed volume, and fractionated by charging 75° C. hot water at a flow rate of SV 0.4 through the column and the high-maltose fraction, with a maltose content of 93 % or higher, was recovered. The results are given in Table II.

The experimental results, as shown in Table II, confirm that when the maltose content in the feed starch sugar solution is 70% or higher, a high-maltose fraction with a maltose content of 93% or higher is easily obtainable in an extremely high yield, i.e. 80% or higher, against the maltose constituent in the feed starch sugar solution.

TABLE I

| | Sugar composition (%) | | |
|---|---|---|---|
| A | B | C | D |
| Maltrup | 7.1 | 48.0 | 44.9 |
| Malstar | 3.2 | 66.0 | 30.8 |
| HM-75 | 1.0 | 76.8 | 22.2 |
| Sunmalt | 4.3 | 85.0 | 10.7 |
| Maltose H | 0.6 | 91.5 | 7.9 |

Note:
A is the material starch sugar solution (trade name or Registered Trade Mark); B, glucose; C, maltose; and D, maltotriose and higher oligosaccharides.

TABLE II

| A | B | C | D | E |
|---|---|---|---|---|
| Maltrup | 48.0 | 132.2 | 44.2 | control |
| Malstar | 66.0 | 231.7 | 56.3 | control |
| HM-75 | 76.8 | 403.6 | 84.3 | present invention |
| Sunmalt | 85.0 | 483.8 | 91.3 | present invention |
| Maltose H | 91.5 | 548.8 | 96.2 | present invention |

Note:
A is the material starch sugar solution (trade name or Registered Trade Mark); B, maltose content in the feed starch sugar solution (%); C, maltose yield in the high-maltose-fraction (g); D, maltose yield against the maltose constituent in the feed starch sugar solution (%); and E, remarks.

EXPERIMENT 2

Bed depth

Similarly as in Experiment 1, the strongly-acidic cation exchange resin of alkali metal-form was packed in one or two columns to give respective total bed depths in the range of 1–20 m as in Table III.

While keeping the temperature in the columns of different bed depths at 75° C., 45 w/w % aqueous solution aliquots of "Sunmalt", a commercially-available starch sugar powder with a maltose content of 85.0%, Registered Trade Mark of Hayashibara Company, Limited, Okayama, Japan, were admitted to the columns in an amount of 5 v/v % against the bed volume, and then fractionated by charging 75° C. hot water at a flow rate of SV 0.4 through the column and the high-maltose fraction, with a maltose content of 93% or higher, was recovered. The results are given in Table III.

The experimental results, as shown in Table III, confirm that when the bed depth is 7 m or longer, a high-maltose fraction with a maltose content of 93% or higher is easily obtainable in an extremely high yield, i.e., 80% or higher, against the maltose constituent in the feed starch solution.

TABLE III

| A | B | C | D | E |
|---|---|---|---|---|
| 1 | 1 | 114.5 | 30.1 | 56.9 |
| 3 | 1 | 343.5 | 102.1 | 64.2 |
| 5 | 1 | 572.5 | 192.9 | 72.8 |
| 7 | 1 | 801.5 | 324.9 | 87.6 |
| 10 | 1 | 1145.0 | 483.8 | 91.3 |
| 15 | 1 | 1715.5 | 739.3 | 93.0 |
| 20 | 2[6] | 2290.0 | 994.1 | 93.8 |

Note:
A is total bed depth (m); B, number of columns; C, amount of the feed starch sugar solution applied (ml); D, maltose yield in the high-maltose fraction (g); E, maltose yield against the maltose constituent in the feed starch sugar solution (%); and [6] means two columns were cascaded.

EXPERIMENT 3

Fractionation temperature

After packing, the strongly-acidic cation exchange resin of alkali metal-form in columns to give respective bed depths of 10 m, as in Experiment 1, feed starch sugar solution aliquots, prepared similarly as in Experiment 2, were applied thereto, and fractionated similarly as in Experiment 1, except that the columns were kept at different temperatures in the range of 35°–95° C. during the fractionation. The high-maltose fraction, with a maltose content of 93% or higher, was recovered. The results are given in Table IV.

The experimental results, as shown in Table IV, confirm that when the column is kept at a temperature in the range of 45°–85° C.,a high-maltose fraction with a maltose content of 93% or higher is easily obtainable in an extremely high yield, i.e., 80% or higher, against the maltose constituent in the feed starch sugar solution with less browning.

TABLE IV

| A | B | C | D | E |
|---|---|---|---|---|
| 35 | 374.7 | 70.7 | 0.023 | easy |
| 45 | 430.2 | 81.2 | 0.059 | easy |
| 55 | 471.1 | 88.9 | 0.105 | easy |
| 65 | 476.9 | 90.0 | 0.150 | easy |
| 75 | 483.8 | 91.3 | 0.176 | easy |
| 85 | 485.9 | 91.7 | 0.205 | easy |
| 95 | 472.2 | 89.1 | 0.496 | difficult |

Note:
A is the fractionation temperature (°C.); B total yield of sugar constituents with a maltose content of 93% or higher (g); C, maltose yield against the maltose constituent in the feed starch sugar solution (%); D, colorization degree, obtained by measuring the absorbance of the high-maltose fraction in 10 cm cell ($A_{420nm}$–$A_{720nm}$), and reducing the obtained value into that in 30 w/w % solution, and E, decolorization using 0.1% activated carbon against sugar constituents.

Several embodiments of the invention are disclosed hereinafter.

EXAMPLE 1

A feed starch sugar solution was prepared by diluting "HM-75", trade name of a commercially-available starch sugar syrup with a maltose content of 76.8%, a product of Hayashibara Company, Limited, Okayama, Japan, in water to give a concentration of 45 w/w %.

"XT-1022E ($Na^+$)", a commercially-available strongly-acidic cation exchange resin of alkali metal-form, a product of Tokyo Chemical Industries, Kita-ku, Tokyo, Japan, in an aqueous suspension, was packed in four jacketted stainless steel columns, inside diameter, 5.4 cm, to give respective bed depths of 5 m, and the columns were cascaded to give a total bed depth of 20 m.

While keeping the temperature in the columns at 55° C., the feed starch sugar solution was admitted thereto in an amount of 5 v/v % against the bed volume, and then fractionated by charging 55° C. hot water at a flow rate of SV 0.13 through the columns and the high-maltose fraction, with a maltose content of 93% or higher, was recovered.

The high-maltose fraction contained 808.2 g maltose, and the yield was extremely high, i.e., 84.3%, against the maltose constituent in the feed starch sugar solution.

EXAMPLE 2

A feed starch sugar solution was prepared by dissolving "Sunmalt", a commercially-available starch sugar powder with a maltose content of 85.0%, Registered Trade Mark of Hayashibara Company, Limited, Okayama, Japan, in water to give a concentration of 60 w/w %.

The resin, used in Example 1, was converted into $K^+$-form in the usual way and packed in a jacketted stainless steel column, inside diameter, 2.2 cm, to give a bed depth of 10 m.

While keeping the temperature in the column at 60° C., the feed starch sugar solution was admitted thereto in an amount of 3 v/v % against the bed volume, and then fractionated by charging 60° C. hot water at a flow rate of SV 0.2 through the column and the high-maltose fraction, with a maltose content of 93% or higher, was recovered.

The high-maltose fraction contained 65.7 g maltose, and the yield was extremely high, i.e., 88.3% against the maltose constituent in the feed starch sugar solution.

EXAMPLE 3

A feed starch sugar solution was prepared by dissolving "Sunmalt", a commercially-available starch sugar powder with a maltose content of 85.0%, Registered Trade Mark of Hayashibara Company, Limited, Okayama, Japan, in water to give a concentration of 45 w/w %.

"Dowex 50WX4 ($Mg^{2+}$)", a commercially-available strongly-acidic cation exchange resin of alkaline earth metal-form, a product of Dow Chemical Company, Midland, Mich., U.S.A., in an aqueous suspension, was packed in fresh columns of the same material and dimensions as used in Example 1 to give a total bed depth of 15 m.

While keeping the temperature in the columns at 75° C., the feed starch sugar solution was applied thereto in an amount of 6.6 v/v % against the bed volume, and then fractionated by charging 75° C. hot water at a flow rate of SV 0.13 through the columns and the high-maltose fraction, with a maltose content of 93% or higher, was recovered.

The high-maltose fraction contained 913.7 g maltose, and the yield was extremely high, i.e., 87.1%, against the maltose constituent in the feed starch sugar solution.

EXAMPLE 4

In this example, a dual-stage fractionation was carried out.

The first fractionation was carried out as follows. Similarly as in Example 1, a feed starch sugar solution was applied to a column, and fractionated except that the feed starch sugar solution was applied to the column in an amount of 20 v/v % against the bed volume. The elution pattern is given in the drawing, where Fractions A through E show a high-dextrin fraction, a high-dextrin.maltose fraction, a high-maltose fraction, a high-maltose.glucose fraction, and a high-glucose fraction respectively, and where the elution is effected in the given order. Fraction C, the high-maltose fraction, was recovered, and Fractions A and E were removed from the fractionation system.

The additional fractionation was carried out as follows. Fraction B, the feed starch sugar solution in an amount of about 10 v/v % against the bed volume, and Fraction D were admitted into the column successively in the given order, and the column then charged with 75° C. hot water, as in Example 3, to effect fractionation. The high maltose fractions, with a maltose content of 94%, were recovered. The additional fractionation was repeated up to 30 batches in total, and the averaged results per batch were calculated. On an average, one high-maltose fraction contained 1483 g maltose, and the yield was extremely high, i.e., 93.3%, against the maltose constituent in the feed starch sugar solution.

EXAMPLE 5

A feed starch sugar solution was prepared by dissolving "Maltose H", trade name of a commercially-available starch sugar powder with a maltose content of 91.5%, a product of Hayashibara Company, Limited, Okayama, Japan, in water to give a concentration of 45 w/w %.

"Amberlite CG-120 ($Ca^{2+}$)", a commercially-available strongly-acidic cation exchange resin of alkaline earth metal-form, a product of Rohm & Haas Company, Philadelphia, Pa., U.S.A., was packed in fresh columns of the same material and dimensions as used in Example 1 to give a total bed depth of 10 m.

Also, in this Example, a dual-stage fractionation was carried out. The first fractionation was carried out as follows. While keeping the temperature in the columns at 80° C., the feed starch sugar solution was applied thereto in an amount of 20 v/v % against the bed volume, and then fractinated by charging 80° C. hot water at a flow rate of SV 0.6 through the columns to obtain a similar elution pattern as in Example 4. Similarly as in Example 4, Fraction C, the high-maltose fraction, was harvested, and Fractions A and E were removed from the fractionation system.

The additional fractionation was carried out as follows. Fraction B, the feed starch sugar solution in an amount of 10 v/v % against the bed volume, and Fraction D, were admitted into the column successively in the given order, and the column then charged with 80° C. hot water at a flow rate of SV 0.6 to effect fractionation. The resultant high-maltose fractions, with a maltose content of 96% or higher, was recovered. The additional fractionation was repeated up to 100 batches in total, and the averaged results per batch were calculated. On an average, one high-maltose fraction contained 1084 g maltose, and the yield was extremely high, i.e., 95%, against the maltose constituent in the feed starch sugar solution.

We claim:

1. A process for the separation of maltose from a feed solution by the utilization of an ion exchange resin, comprising:
   (a) providing a feed solution containing at least 70% maltose based on the weight of the dry solid, the remainder consisting essentially of glucose and dextrins;
   (b) sequentially admitting predetermined volumes of the feed solution and water to a column of a strongly acidic cation exchange resin having sulphonyl groups of an alkali metal or alkaline earth metal form;
   (c) sequentially separating the effluents from the column into the following fractions:
   a first fraction rich in dextrins,
   a second fraction rich in dextrins, but highly contaminated with maltose,
   a third fraction of substantially pure maltose,
   a fourth fraction rich in maltose, but highly contaminated with glucose, and
   a fifth fraction rich in glucose;
   (d) recovering the third fraction of substantially pure maltose;
   (e) sequentially admitting into the column;
   the second fraction obtained in the step (c),
   a feed solution having a maltose content of at least 70% based on the weight of dry solid, and the remainder consisting essentially of glucose and dextrin,
   the forth fraction obtained in the step (c), and water; and
   (f) repeating steps (c), (d) and (e) in a cyclic manner.

2. A process in accordance with claim 1, wherein the maltose content in the third fraction is 93% or higher, based on the weight of the dry solid.

3. A process in accordance with claim 1, wherein the bed depth of the column is at least 7 m.

4. A process in accordance with claim 1, wherein the temperature of the column of the resin is kept at 45°-85° C.

5. A process in accordance with claim 1, wherein the cation exchange resin is in the form of $N^+$, $K^+$, $Ca^{2+}$, or $Mg^{2+}$.

6. A process in accordance with claim 1, wherein the concentration of the dry solid solute in the feed solution is in the range of 10-70 w/w %.

7. A process in accordance with claim 1, wherein the water is admitted to the column at a flow rate of SV 0.1-2.0.

* * * * *